United States Patent

Wagher

Patent Number: 5,453,007
Date of Patent: Sep. 26, 1995

[54] ELASTIC DENTAL IMPLANT

[76] Inventor: Felix Wagher, 56 South St., Danbury, Conn. 06810-8154

[21] Appl. No.: 278,916

[22] Filed: Jul. 22, 1994

Related U.S. Application Data

[63] Continuation-in-part of Ser. No. 44,122, Apr. 8, 1993, abandoned.

[51] Int. Cl.$^6$ .............................. A61C 8/00; A61C 13/12; A61C 13/225
[52] U.S. Cl. ............................................. 433/177; 433/173
[58] Field of Search ................... 433/172, 173, 433/174, 175, 176, 177

[56] References Cited

U.S. PATENT DOCUMENTS

| | | | |
|---|---|---|---|
| 4,475,890 | 10/1984 | Heidelbach | 433/173 |
| 4,525,145 | 6/1995 | Scheicher et al. | 433/173 |
| 4,552,532 | 11/1985 | Hozsary | 433/173 |
| 4,568,285 | 2/1986 | Chiaramonte | 433/169 |
| 4,713,006 | 12/1987 | Hakamatsuka et al. | 433/173 |
| 4,881,897 | 11/1989 | Franek et al. | 433/169 |
| 4,938,693 | 7/1990 | Bulakiev | 433/169 |
| 4,950,161 | 8/1990 | Richter | 433/173 |
| 4,957,437 | 9/1990 | Shimura et al. | 433/169 |
| 5,026,280 | 6/1991 | Durr et al. | 433/175 |
| 5,049,073 | 9/1991 | Lauks | 433/169 |
| 5,114,343 | 5/1992 | Musikanti et al. | 433/169 |
| 5,174,755 | 12/1992 | Fukuda | 433/173 |

Primary Examiner—Nicholas D. Lucchesi

[57] ABSTRACT

A system of uniquely interchangeable dental implant insert elements which may be readily interchanged by screwing the removable elements into and out of a stationary osseointegrated dental implant housing. The removable insert elements may vary as to their rate and degree of elasticity. The abutment shaft upon which the dental prosthesis is affixed is of standard size throughout the system, and is splined in such a way that the splines can be engaged by a single insertion/removal instrument. The overall design is such that the proper degree of shaft deflection for each case can be readily and painlessly tried in until the desired result is obtained. The inserts are designed to be retrievable at any time allowing for removal and replacement of the existing prosthesis which is affixed to the insert. The insert elements can be continuously interchanged throughout the patient's lifetime to allow for changes in the patient's dental needs. The unique design of these inserts allows the dentist to compensate for slight misalignment problems when trying to obtain multiple coincident paths of insertion by allowing the abutment bearing shaft to be deflected such that the longitudinal axis of the shaft can be made to coincide with the path of insertion of the prosthesis, and thus greatly facilitate the seating and restoration of the prosthesis.

8 Claims, 9 Drawing Sheets

ELASTIC DENTAL IMPLANT

This application is a continuation-in-part of Ser. No. 08/044,122, filed Apr. 8, 1993 and now abandoned.

BACKGROUND OF THE INVENTION

The ideas for this invention stem from the inventors work with and experience in the placement and subsequent fabrication of a prostheses on rigid dental implants. The inventor is a practicing dentist In recent years, several designs for single tooth dental implants have appeared. However, a rigid endosseous dental implant exhibits little or no axial deflection, as would a naturally occurring tooth. Therefore, failure rates of prostheses which were abutted to both endosseous implants and naturally occurring teeth were high. Flexible implants are beginning to appear. These implants are designed to lessen the stress on the bony tissues directly adjacent to the endosseous implant. The design of this standardized system of removable dental implant insert elements is to address the problem of ascertaining the correct degree of elasticity required to clinically manage the several specific demanding areas of successful implant dentistry and long term case management.

The problems encountered are several. First, is one of non uniform stress, which may manifest itself in several ways. The phenomenon of non uniform stress is observed when a rigid prosthesis is affixed to a rigid implant and a natural tooth, which has some degree of movement. Under occlusal forces, compressive forces (as well as tensile forces) with lateral components in any direction are encountered.

Since the rigid implant cannot follow the tooth through the range of motion, non uniform stresses are transferred from mastication through the prosthesis, and onto the implant and tooth. Catastrophic failure is often the result. Failure may occur at a critical solder joint on the prosthesis, or at the site of the implant/bone interface, in the implant itself, or, most commonly, at the site of the natural tooth/ bone interface. The catastrophic failure of any element of the prosthesis or its abutments results in loss of the entire restoration.

However, an even more common problem occurs when placing a posterior implant which turns out to be misaligned (FIG. 6). One of the most difficult problems in implant dentistry is the fabrication of the final prosthesis. Even recently developed elastic implants do not address the problem of non coincident paths of insertion among multiple abutments (FIGS. 6 & 7), nor the fact that as case types change, requirements of elasticity change. The design of this invention is to solve both of these problems by means of a series of elastic implant elements which can be interchanged to allow alignment of multiple paths of insertion and be replaced easily to accommodate changing needs to the patient without removal of the stationary endosseous element itself.

DESCRIPTION OF THE PRIOR ART

The applicant cites the most recent of these by Fukada, U.S. Pat. No. 5,174,755, and Durr et al., U.S. Pat. No. 5,026,280.

Neither implant has an axis of rotation which is deep in bone, but both are limited to axes at or above the level of osseous tissue.

Neither implant addresses the rate or limits of flexibility, much less what those rates or limits should be.

U.S. Pat. No. 5,174,755 by Fukada et al., describes an implant which has a supra osseous axis of rotation which is entirely inconsistent with that of a natural tooth. One would therefore expect it to exhibit failure due to shear stress at the level of the un reinforced elastic media Also, there is no tendency towards bodily returning the abutment shaft towards its neutral or unstressed position other than the unreinforced media itself. One would expect the elastic to simply come to a new equilibrium position. In fact most of the references found are directed towards reducing bone stress at the implant site, and natural tooth abutments and prostheses are not addressed.

The same argument applies to the Durr et al. implant, which does acknowledge the different vertical and lateral deflection aspects, but in a nonspecific manner. One strong and serious limitation of the Durr implant is that the prosthesis cannot be affixed rigidly to the abutment. The sliding sleeve is the whole principal for the vertical component of motion, and is a glaring problem. For example, if the prosthesis was designed to cantilever past the Durr implant, and occlusal stress was applied to the opposite side, the entire apparatus would easily become disengaged, but not before transferring all stress to the natural tooth. This amount of stress would easily shear the tooth through the root.

Musikanti et al. in U.S. Pat. No. 5,114,343 employs a spring like device located below the tooth supporting structure and the tooth supporting structure is grooved at the open end. The applicant believes this to be a poor design because upon placement into the oral cavity, this chamber will fill with saliva plaque, bacteria and particles of food debris which would tend to foul the mechanism. Galvanic reaction may occur between a different metal than that from which the invention is made because of intimate contact between adjoining metal parts. This will manifest itself either as pain to the patient ( as which sometimes occurs between gold and silver restorations when they are in intimate contact and saliva is present). Alternately, galvanic reaction may serve to degrade the structural integrity of the prosthesis, especially at solder joints, precision attachments, etc. The device is not readily adjustable as to degree and rate of deflection.

In the design of U.S. Pat. No. 4,525,145 by Scheicher et al., it appears that once the apparatus is assembled, the entire apparatus may be irretrievable once the external aspect of the endosseous implant component became osseointegrated. But even if the separate internal components could be removed (and there is no specification as to if or how this could be accomplished), the degree of lateral and vertical flexibility requires extensive disassembly and readjustment of the internal components and then reinserting the apparatus in a trial and error fashion. First, the extensive and repetitious handling of these components in a real chairside clinical environment would certainly tend to increase chances for the introduction of infection directly into the area of the implant, which has been widely accepted by the dental community as undesirable.

Secondly, it does not appear that the components of the internal aspect are meant to be retrieved after the introduction of the implant. In the event of loss of another abutment or progressive periodontal disease or even the use of an externally located orthodontic device as a preprosthetic adjustment, it would be extremely time consuming and difficult to effect the aforementioned adjustments intraorally.

Another disadvantage of the Scheicher et al. implant is that repeated assembly and disassembly of such precision parts to achieve the precise degree of flexibility desired may lead to wear and contribute to premature failure of the mechanism, or inadvertent omission of parts, which would almost certainly lead directly to catastrophic failure of the apparatus, and possibly the loss of the entire prosthesis supported on it. there is no clear provision for removing the prosthesis for servicing the implant mentioned in either invention. Depending on the materials chosen, the possibility of galvanic reaction is also present here.

SUMMARY OF THE INVENTION

The applicant's proposed invention would do away with this extensive and time consuming chairside disassembly by virtue of the fact that it is an integrated system of interchangeable "one piece" inserts of readily packaged and presterilized inserts with the degree of lateral and vertical flexibilities listed on each individual insert's package.

Clinically, the stationary element could be clinically placed in any of the desired methods, including threaded, press fit, parallel or tapered sided, etc. and covered over with a healing cap 30 in place (FIG. 4).

The first unique feature of the proposed invention is that the design allows for the application of rotational force to be applied to the abutment shaft 5 which by means of splines 6 and lateral deflection limiting collar 8 transfers said rotational force through the elastic media matrix onto the retentive protuberances 3 and the removable insert 2, also called the removable element 2. This may be accomplished without permanent structural deformation of the elastic media or any of its associated components. Simply stated, a wrench like means (one possible embodiment is depicted in FIG. 8, as #24) is employed to make placement or retrieval of the elastic implant element (26) easier and quicker for the clinician.

In a case where the clinician wishes to match a degree of flexation in existing teeth, the patient would occlude on a thermoplastic laminated bite registration wafer 29 (FIG. 10), the specifications for which are enclosed. By interpreting the degree of displacement of the thermoplastic media in the area adjacent to the proposed implant site, the proper degree of lateral and vertical displacement may be very closely approximated. this would eliminate a great deal of trial and error.

If the clinician finds that adjustments are required for reasons of alignment or patient comfort, the desired element can be readily selected and quickly and easily inserted without the need for anesthesia. In the future, if flexibility needs should change, each element can be readily exchanged for another of different compressive, lateral, or both deflections.

In the case of minimally misaligned implants as in FIG. 6 with other implants or naturally occurring teeth, the clinician can easily insert the element with the proper amount of flex to induce a coincident path of insertion. The inventor also proposes that because of the unique construction of the interchangeable elastic insert, that due to the inherent tendency of the shaft to return to the central unstressed position, and the unique axis of rotation, that the insert will tend to orthodontically reposition itself so as to align with the path of insertion of the prosthesis. This represents a simple tipping rotation of the lower implant housing in bone which is induced by the elastic tendency of the shaft in my unique insert to revert to the neutral unstressed position. This self aligning feature should not be abused or used to accomplish large corrections but only to compensate for alignment problems within the conical envelope of motion. This orthodontic self alignment relies on proper anchorage to other healthy teeth as abutments to dissipate the reactive force, as in any orthodontic movement.

In the case of more substantial alignment problems, the interchangability of inserts can be exploited as follows. With the aid of an easily fabricated prosthesis (FIG. 8), the integrated implant system can be used in the following way: First use the largest degree of flexibility required to align the abutment shaft. Second, allow the internal stresses of the self centering shaft to orthodontically reposition the shaft (FIGS. 8 and 9). As the implant moves into position, elements with lesser degrees of lateral and vertical flex may be substituted to maintain movement and increase the amount of stress transmitted into the surrounding bone until proper orthodontic alignment (FIG. 9) is achieved.

Having performed an in depth analysis of the aforementioned patents, and several others before them, The applicant has not found evidence of a system of standardized interchangeable elastic implant inserts which can be reliably and easily exchanged without surgery or discomfort in a general practitioner's setting.

One of the most significant improvements of this proposed system is that it introduces an element of clinical "forgiveness" which has made many dental practitioners reluctant to recommend them to patients who would benefit tremendously. However, until this invention, a misaligned or incorrect type of implant meant great difficulty for the dentist, lab technician and most especially, the Patient.

Prior to this proposed invention, the remedy for the above problem is either pre prosthetic orthodontic treatment to align the path of insertion for the implant, or a telescopic crown. A telescopic crown is a coping affixed to the implant, the coping is then used to change the effective path of insertion so that the prosthesis can be affixed over both the coping and implant. This is undesirable because it introduces greater complexity (and therefore likelihood of failure) into an already very complex design.

However, the elastic element and unique envelope of motion in the proposed invention makes it possible to deflect the shaft of the insert to achieve parallelism in three dimensions, and as such facilitates insertion of the prosthesis. In this way, minor differences can be resolved, and the degree of difficulty for the clinician and laboratory (and thus, the patient!) is effectively reduced manifold.

The introduction of a standardized removable elastic insert also serves to increase maintainability and reliability. In the event of failure of any of the internal components, a new insert can be simply and quickly inserted.

I further propose a system of standardized elastic inserts which has distinct increments of deflection. For example, lateral limits of 0.2 mm., 0.4 mm., 0.6 mm., etc. and vertical compressive rates of, for example 0.1 mm., 0.2 mm., 0.3 mm. This would allow a system where the insert may be readily stored in drawers marked 0.2 mm. lateral/0.1 mm. vertical. color coding may further facilitate the bulk storage method.

Finally, I propose a "gauge" for the determination of the vertical compressive requirement which could be composed of a laminated wafer of low fusing thermoplastic materials of different viscosities. The "harder" laminations would be placed at the center, and successive layers would get softer as they progress outward. These laminations would be of a different color for each layer. The colors would be keyed to the implant color codes.

The aforementioned wafer would be placed in the mouth over the prosthesis at the try in stage. The patient would be asked to occlude on the wafer and the depth of displacement of the laminations would be read. Then, the appropriate element would be inserted until the penetration of the laminations was the same over natural teeth as over implant abutments.

DETAILED DESCRIPTION OF PREFERRED EMBODIMENTS

Figure 1:
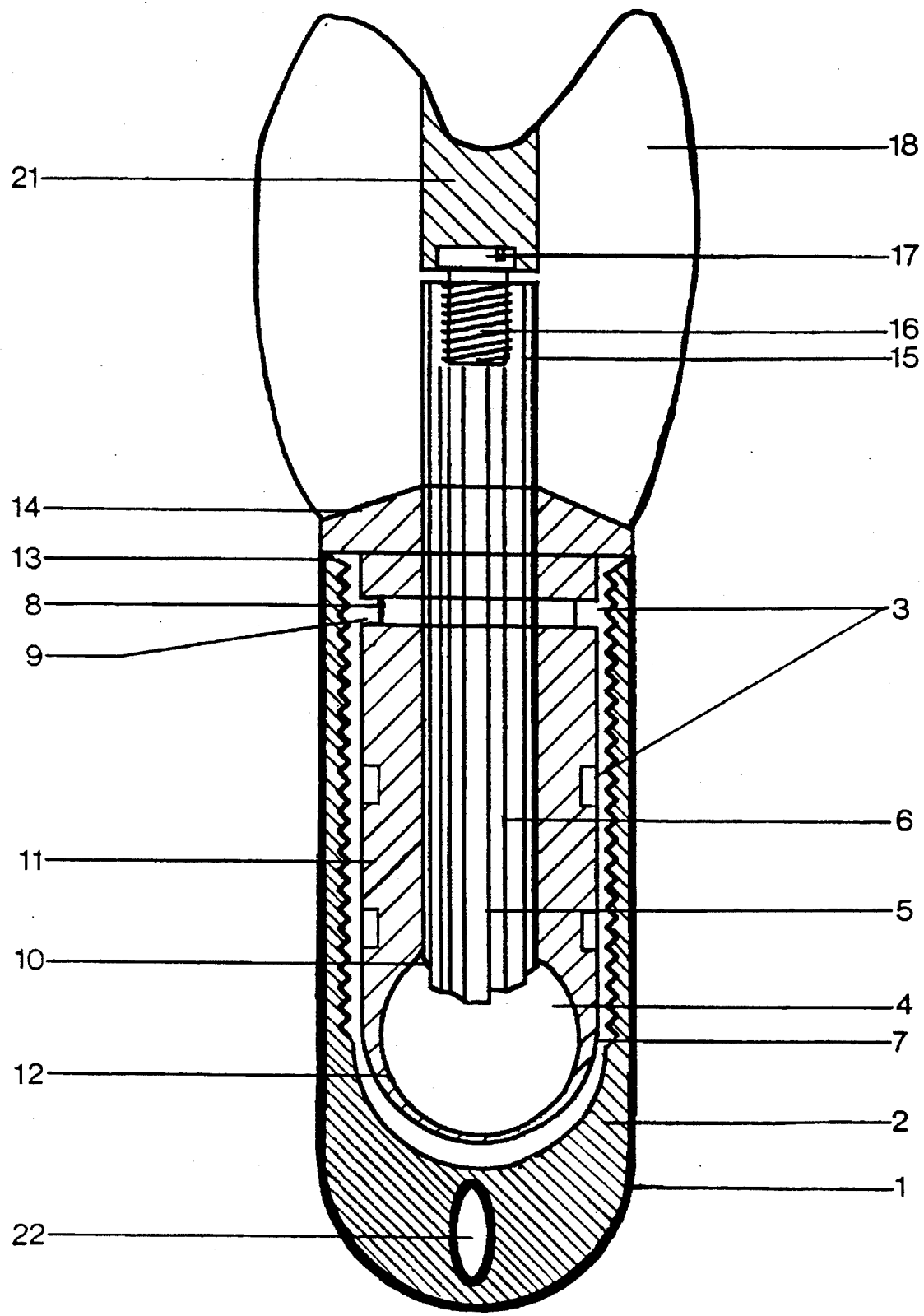
FIG. 1 is a sectional view of the implant system of the present invention.

In FIG. 1, drawings, one possible embodiment is depicted for purposes of clarity and explanation of parts and features. Items shown in drawing are as follows:

The outer implant housing 1 which represents a modified outer endosseous dental implant structure. Housing 1 is depicted here as being composed of a rigid biocompatible material such as, but not limited to, titanium with the outer aspect coated in hydroxylapetite where it will contact osseous tissue. The internal aspect of housing 1 is machined into a sphere at the closed end, and threaded along the remainder of the internal aspect.

Figure 2:
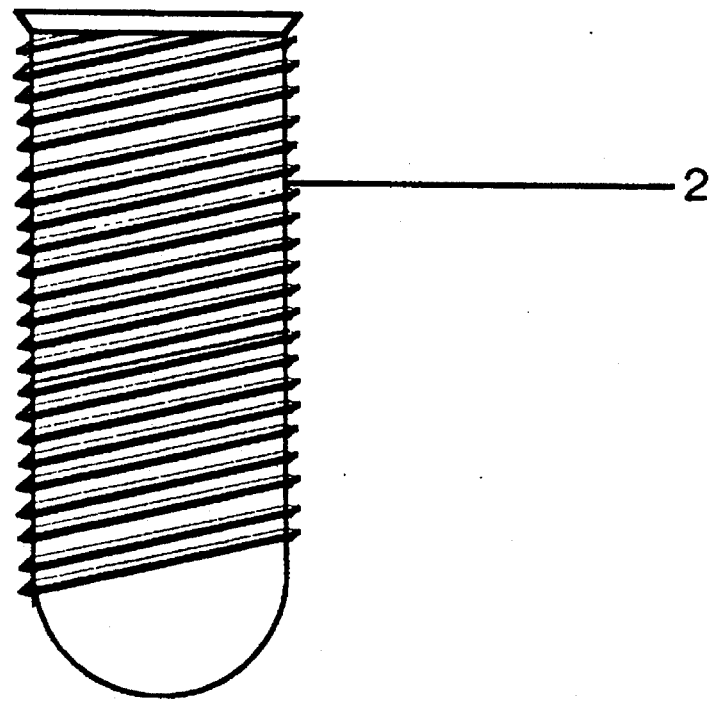
FIG. 2 is an exploded view showing first and second cylindrical members.
Figure 2:
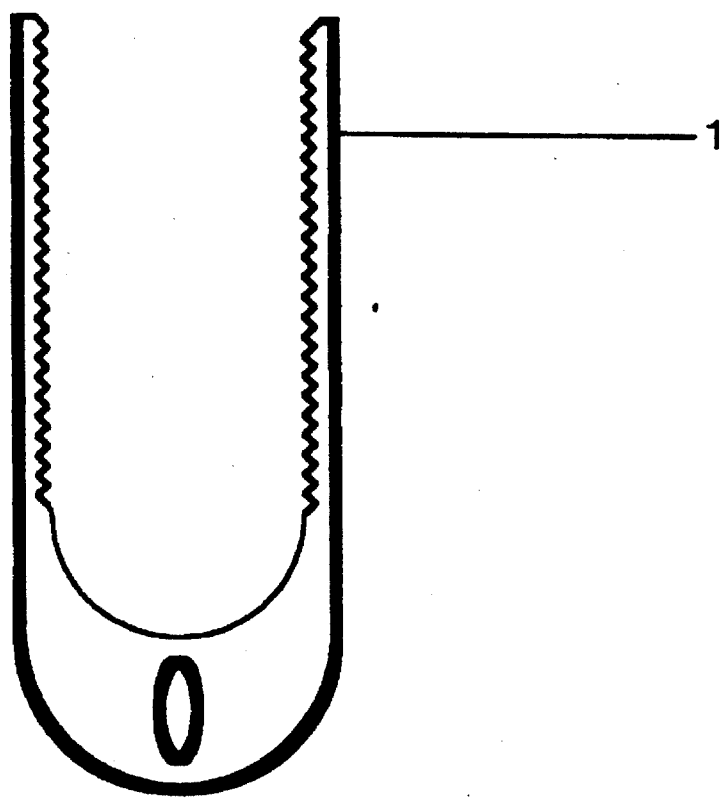

Removable element 2 is also depicted as being machined from a strong, rigid material, such as, but not limited to titanium. There are cooperating threads on the external aspect of element 2, and thusly, element 2 and the contents of element 2 may be inserted and rigidly affixed into housing 1 by threading the closed end of element 2 down into housing 1 until seated, which functions here to affix the removable element 2 rigidly to bone as in FIG. 2.

Herein, element 2 and all items contained within its structure will be referred to as the "removable element" 26 of the prosthesis. The outer aspect of element 2 is threaded into housing 1. The inner aspect of element 2 is machined into a spherical shape at its closed end, to act as a support for, a spherical lower retaining globe 4, which is suspended in elastic media 11 (polyoxymethelene for example) at lower end 7 of elastic media 11.

The main abutment bearing shaft 5, is rigidly affixed into the receiving end of the spherical lower retaining globe 4. The end 10 of shaft 5 which is embedded in globe 4 is shaped such that it distributes its vertical compressive load uniformly through globe 4, to the outer aspect 12, across elastic media located at lower end 7, and onto inner aspect of element 2 machined into a spherical shape at its closed end where compressive stress is ameliorated, and evenly dispersed over the larger surface area of the implant housing 1.

The compression in the vertical plane is limited by varying the thickness of elastic imbedding media at lower end 7. This design allows vertical compression rate to be varied independently of lateral deflection rate. This is a key element in this design.

The abutment bearing shaft 5 is a rigid shaft, typically of titanium or sufficiently rigid polymer. Shaft 5 comprises longitudinal splines 6 to retain an upper maximum lateral deflection 8, and to resist rotation in elastic media 11.

Along the mid length of the internal aspect of element 2 are splined retentive protuberances 3 which act to prevent rotation or displacement of elastic media 11 or components retained therein. The splined retentive protuberances 3 cooperate with the splines on the external circumference of limiter 8 such that rotational forces will be distributed from the prosthesis supporting shaft 5 through limiter 8 and onto the protuberances 3, and thus element 2.

In this manner, the entire removable element and contents can be inserted or removed by application of rotational force on shaft 5. Note that the limited flexibility of limiter 8 allows a controlled degree of lateral flexibility of shaft 5 but maintains strict transmission of rotational forces placed on shaft 5 to be transmitted through limiter 8 onto element 2. This is another key element in this design. Note the location of splined protuberances are so as not to contact or interfere with the rotation of the lower retainer 4.

In a second possible embodiment, the outer circumference of limiter 8 is splined in such a fashion as to allow an adequate thickness of elastic media 11 to maintain its structural integrity after repeated cycling. The outermost splined contacting surface of limiter 8. That is, the circumference of the spline face is shaped to follow the inner circumference face of element 2 with a layer of elastic media 11 interspersed between limiter 8 and element 2. The degree and rate of maximum lateral deflection may be achieved by varying the maximum effective circumference of limiter 8, and therefore, the amount of elastic media 11 at the interface 9 between limiter 8 and element 2.

Again it should be noted that the lateral deflection may be independently varied from the degree of vertical compression.

The upper maximum lateral deflection limiter 8, further aids in preventing catastrophic vertical failure under tension because its inner circumference is splined to receive shaft 5, in a rigid and permanent fashion.

In one embodiment, a gingiva penetrating member 14 is threaded into the internal aspect of element 2 at flange 13. Flange 13 has a counter bevel located on the inner aspect of 1 at the open end. The flange 13 has a bevel which will cooperate with the gingiva penetrating member 14. In the preferred embodiment, the gingiva penetrating member may be integral continuous elastic media 11. This would ensure a tight seal against bacterial infiltration between member 14 and shaft 5 as well as housing 1 and element 2.

A second embodiment would have member 14 composed of a flexible biocompatible material such as surgical silicone rubber, Teflon, or equivalent, and serves to allow a tight flexible seal intimate with the splines at the prosthesis mounting end 15 of the prosthesis supporting shaft 5. In this fashion, the deflection of the shaft 5 is allowed to progress unimpeded through its conical envelope of motion.

Optionally is the use of a screw 17 which comprises threads 16 and is threaded into the prosthesis bearing end of shaft 5 for the purpose of easily reversible fixation of said prosthesis 18. Having secured prosthesis, a filling material 21 may be used to occupy the counter bore and prevent foreign object contamination of the fastener assembly. If a screw were used, it is recommended that it be an Allen head, as this type of screw can be carried into place intraorally with less chance of dropping the screw.

Also depicted in this embodiment, but not essential to it, is the use of a fenestration 22 which serves as a means to facilitate osseointegration of the lower implant housing 1. The use of a fenestration for this purpose has been previosly documented in U.S. Pat. No. 4,938,693, by Bulakiev.

Figures 3, 3B:
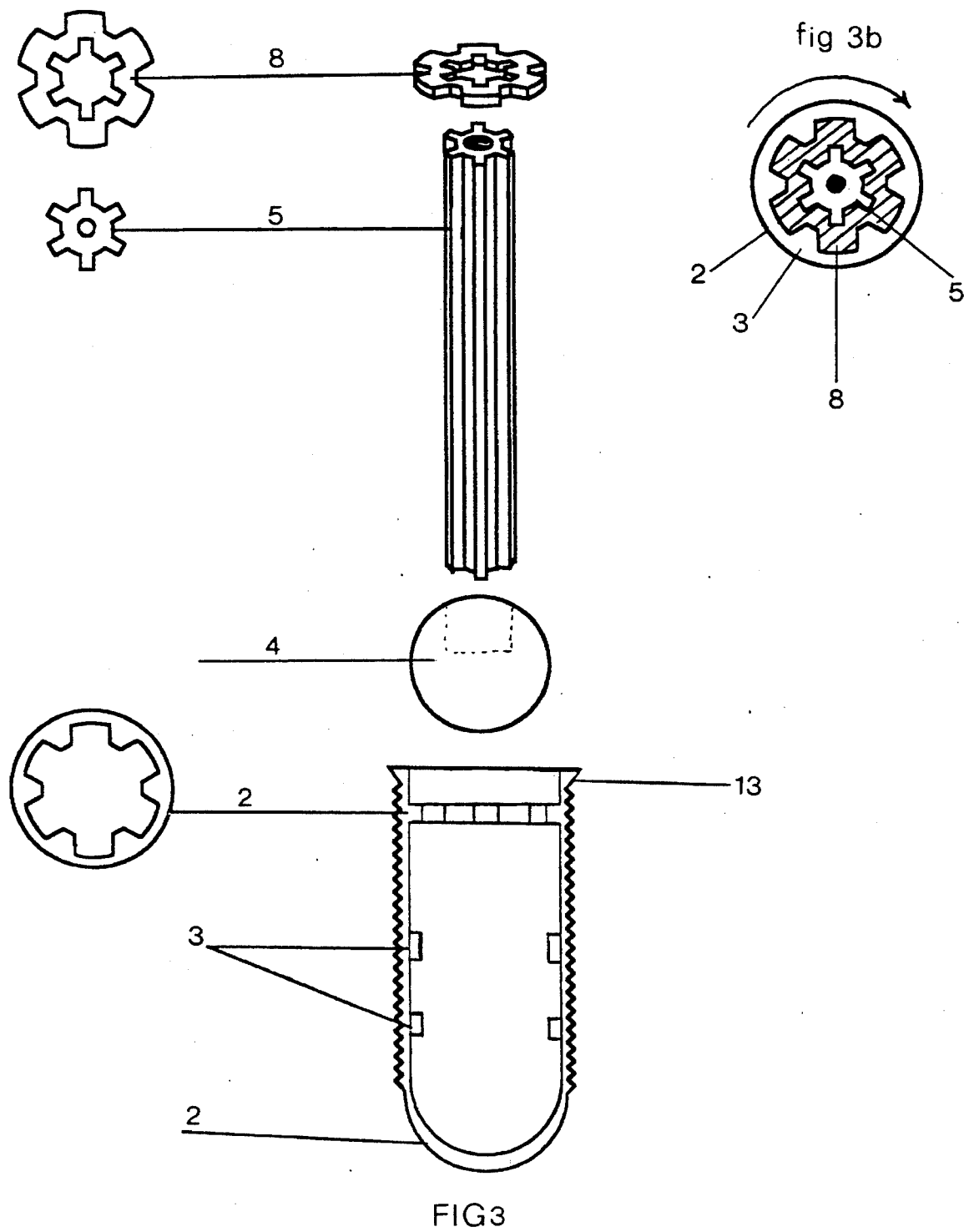
FIG. 3 is an exploded view of the implant system of FIG. 1.
Figure 4:
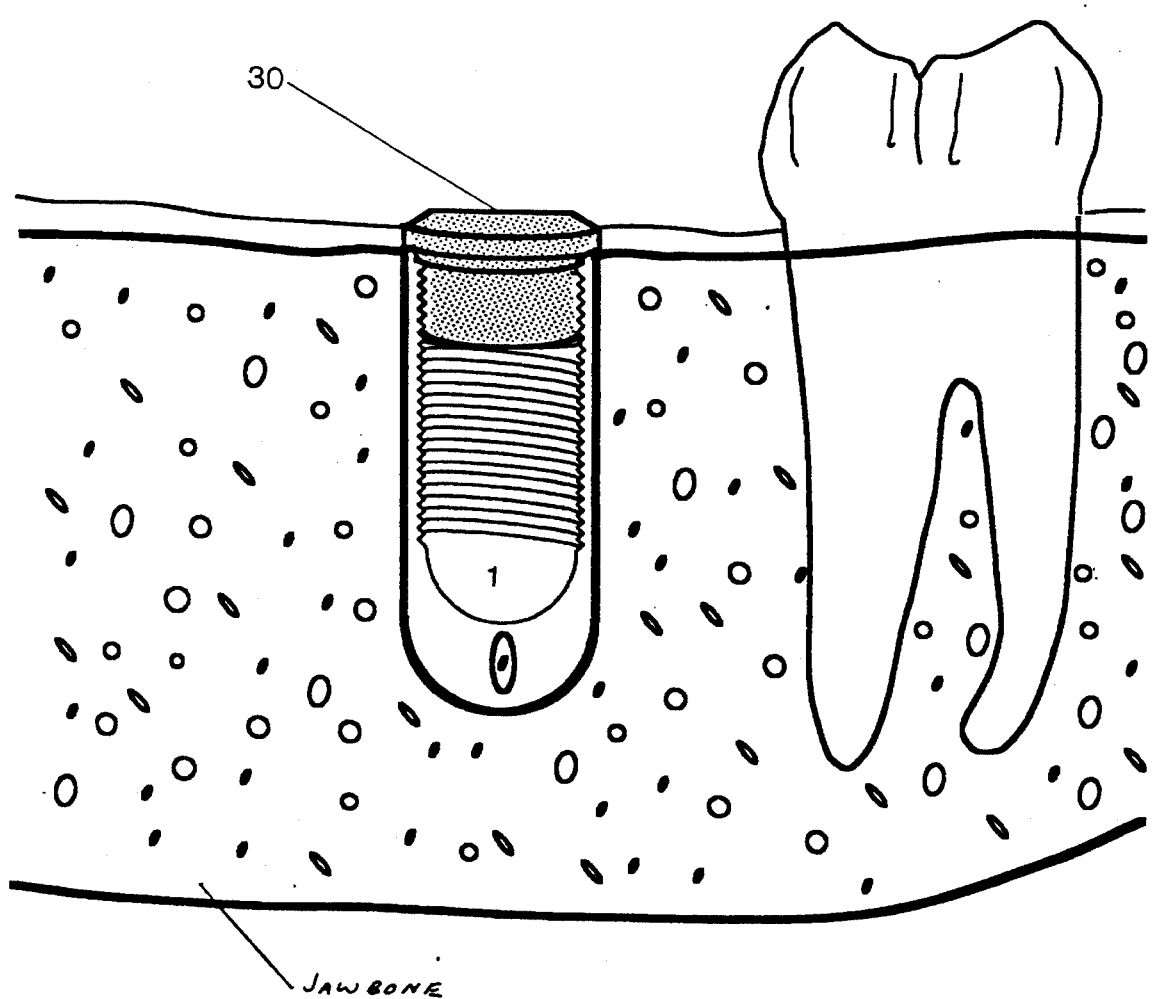
FIG. 4 shows the use of a healing cap with the implant submerged in a jawbone.
Figure 5:
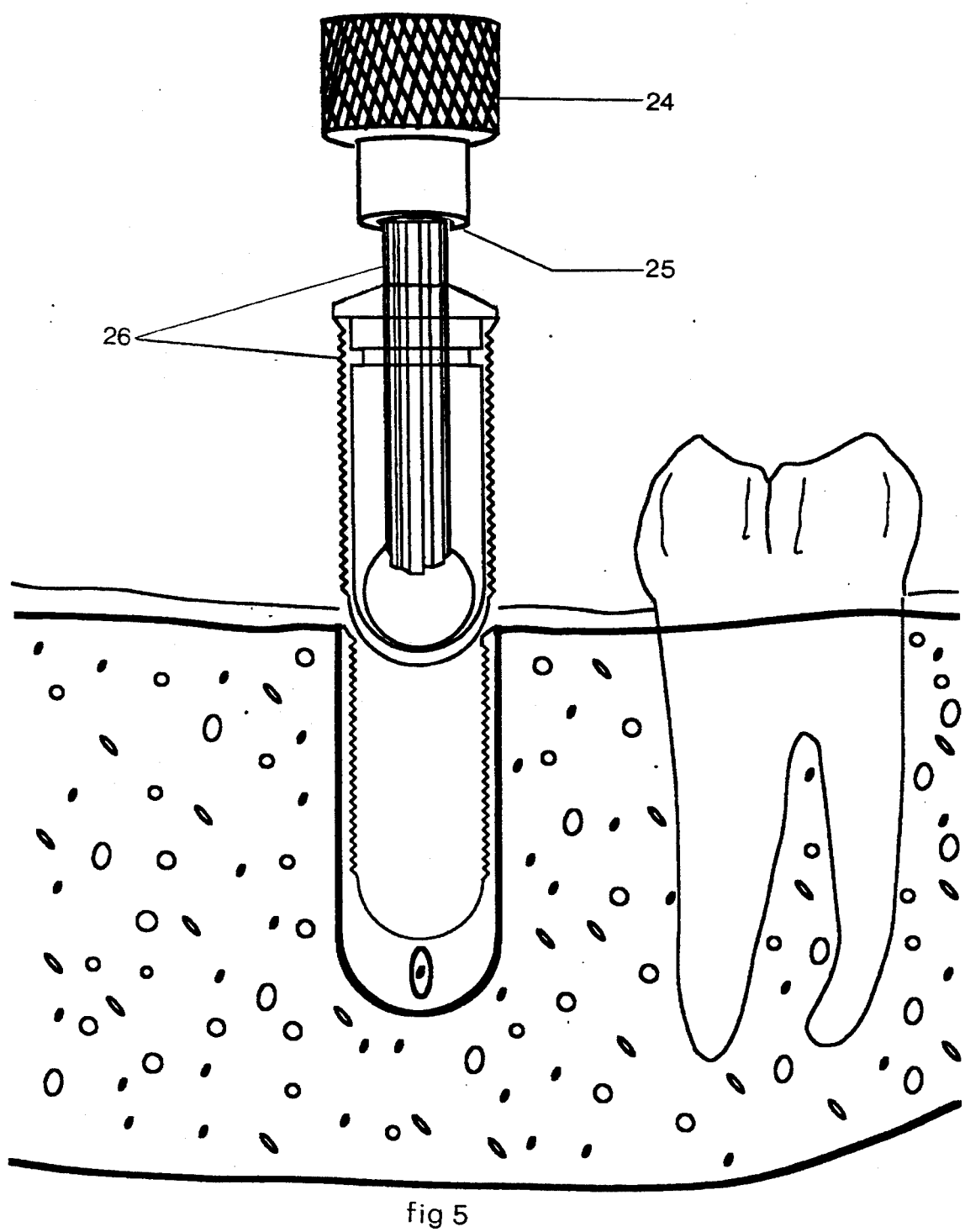
FIG. 5 shows the use of a wrench in disassembly of the implant system.
Figure 6:
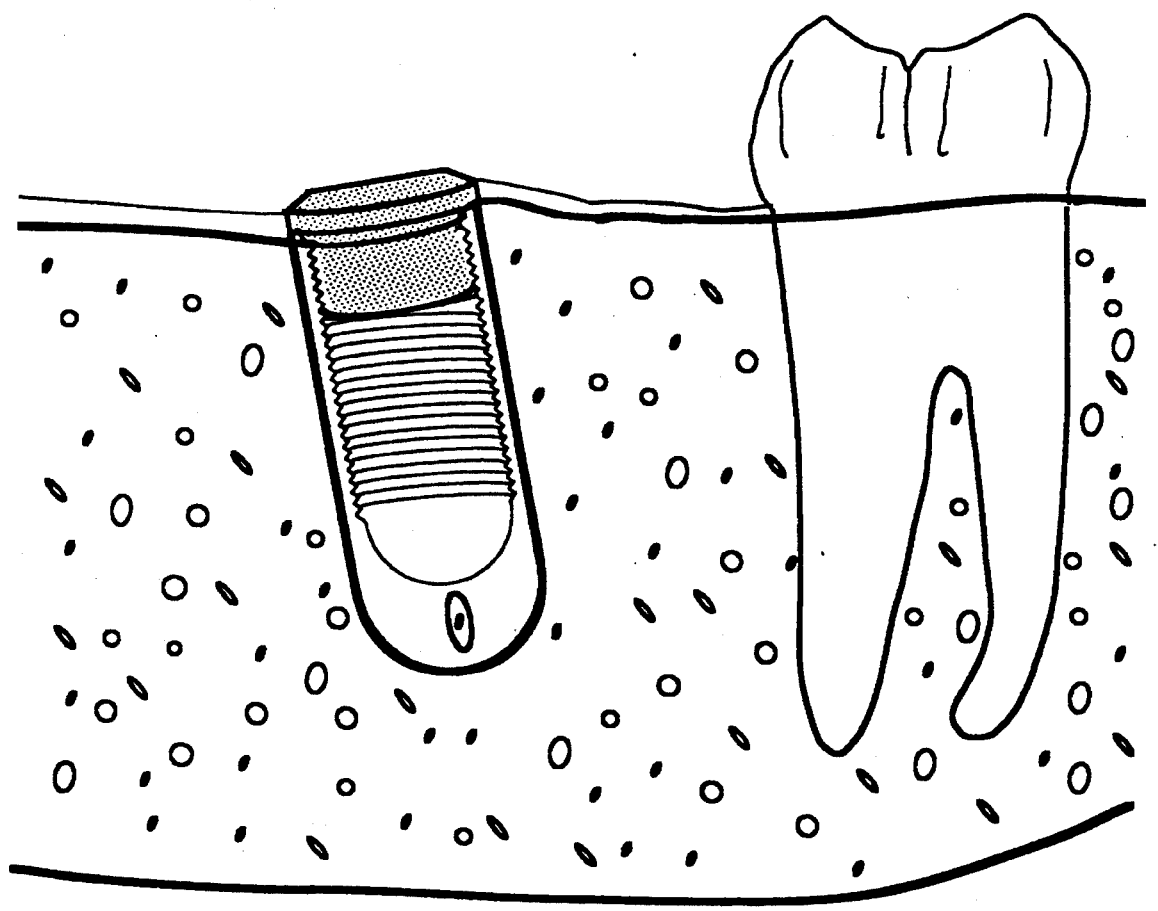
FIG. 6 shows the use of a healing cap in an implant which is misaligned with respect to an adjacent tooth.

Also noted in FIG. 3, is a healing cap 30 which is placed into the open end of housing 1 by means of threaded retention during the period of osseointegration (typically 6 months) to prevent impaction of undesirable debris and aid in healing. Typically constructed of Teflon coated polymer, the use of the healing cap is included only for thoroughness of explanation.

Figure 7:
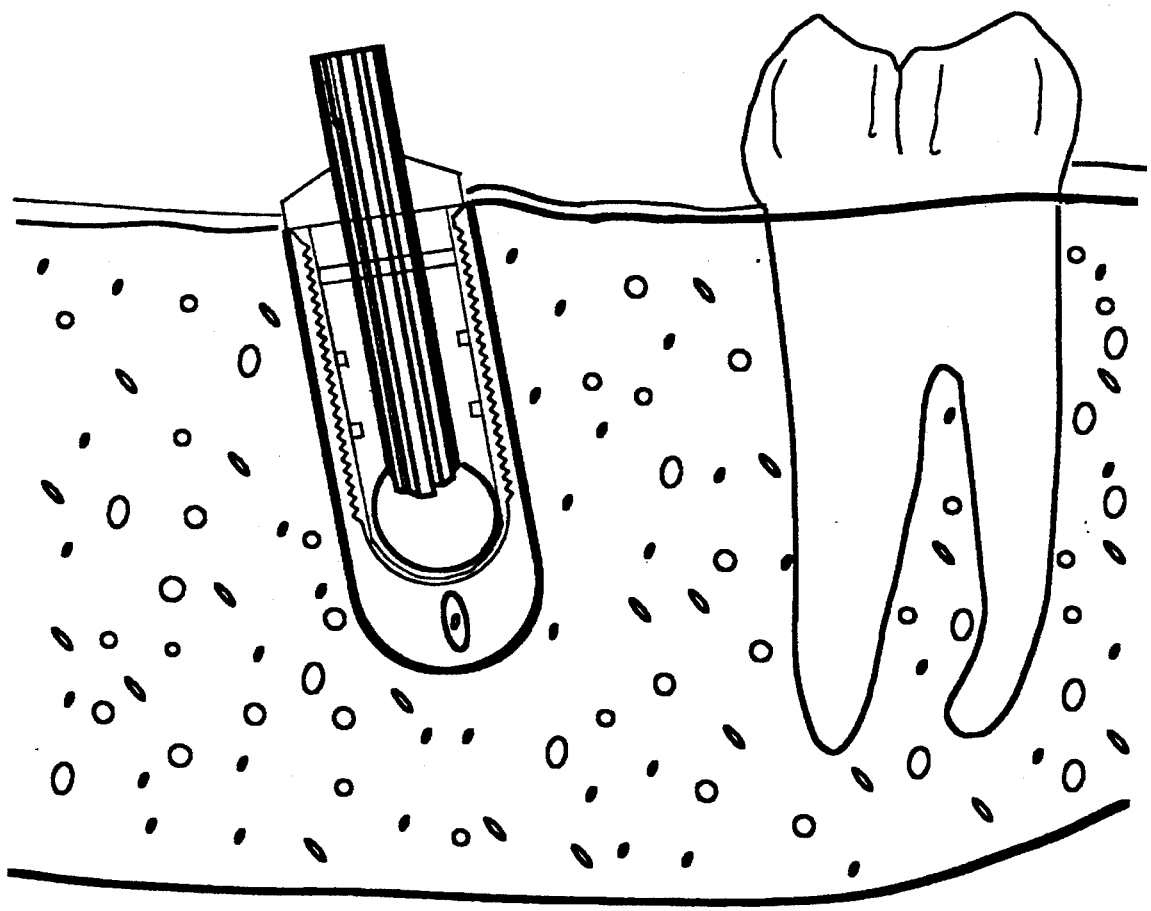
FIG. 7 shows the implant of the invention embedded in a misaligned fashion with respect to an adjacent tooth.

Also depicted for clarity in drawing FIG. 7 is a means 24 of reliably grasping the removable element, here depicted as a cylindrical gnurled grip, which compresses splined 25 cavity to receive the implant bearing shaft head 15 of the removable insert unit 26. As previously stated, the shaft head 15 is a standard design and size for each element, and means 24 serves facilitate interchange of insert element 26 until the insert unit with the desired envelope of motion has been obtained.

The design of the proposed invention allows the placement of rotational forces from grasping areas 24 onto the shaft 15 from which it is translated throughout the elastic media 11 and onto the removable housing 2 by means of the retentive protuberances 3 and thus into the whole of element 2, thus resulting in the ability to thread the entire 26 bodily into or out of housing 1 without internal failure of the media 11 or insert unit apparatus 26.

Figure 8:
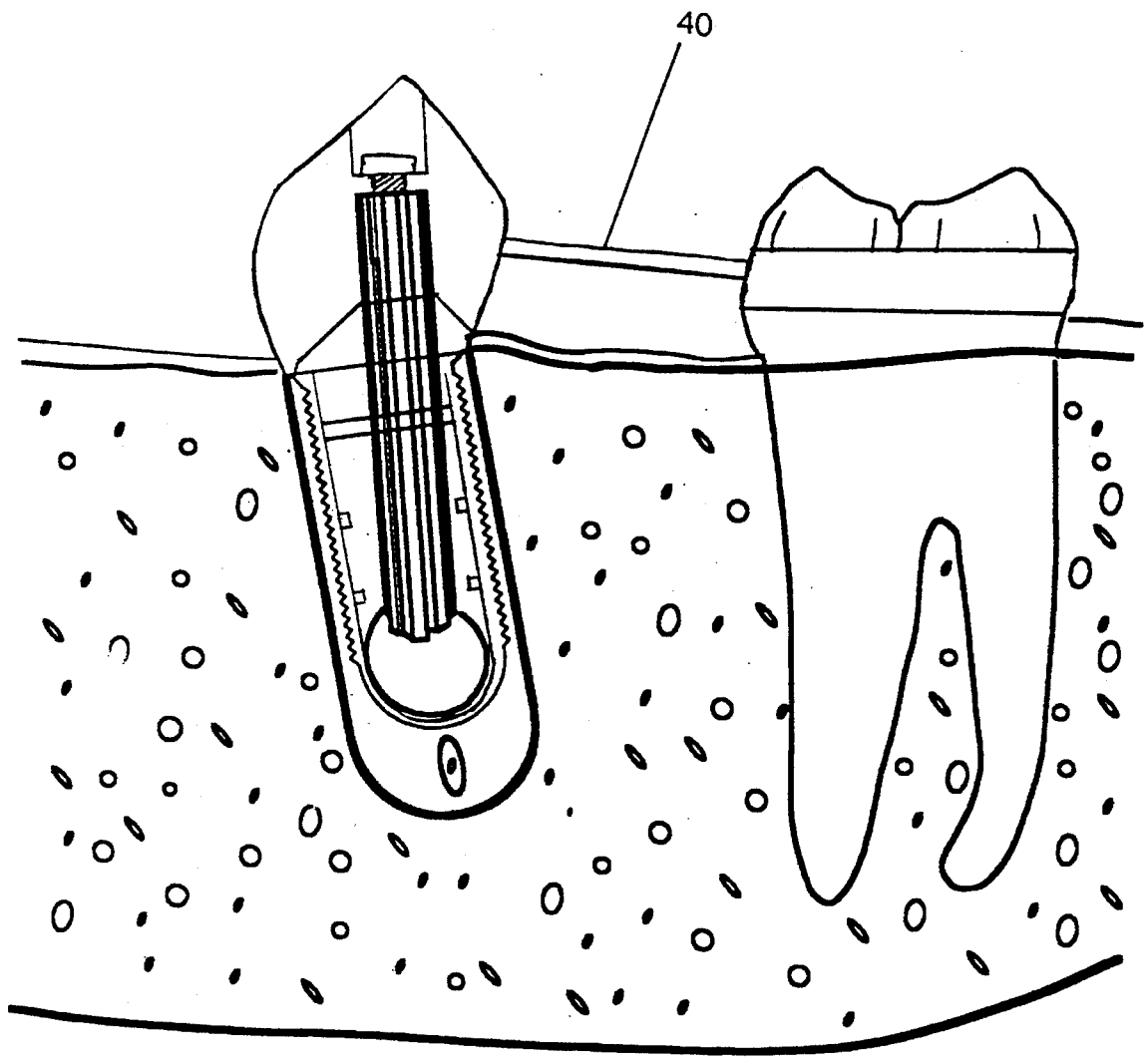
FIG. 8 shows the use of the implant of the invention in conjunction with an orthodontic traction appliance.
Figure 9:
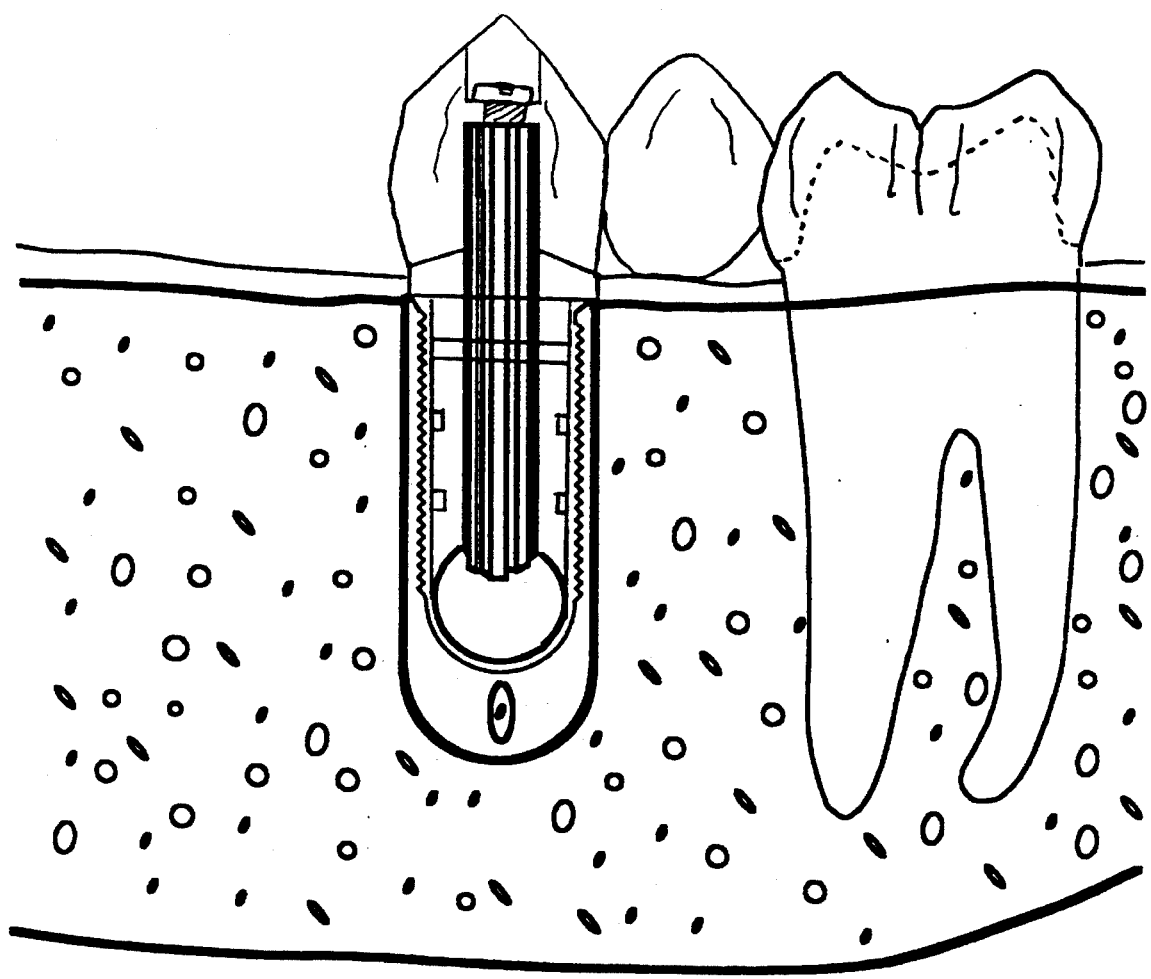
FIG. 9 shows the use of the implant of the invention in the restoration of an edentulous area of the oral cavity.

Further, the design of the invention includes the intentional tendency of shaft 5, and thus the shaft head end 15 of said shaft to return to the central unstressed position. Refer to FIG. 7. The ability of the flexible shaft allows the correction of the condition of non coincident path if insertion as depicted in FIGS. 7 through 9. Further, the construction of the invention allows for the feature of self aligning orthodontic repositioning of both the submerged implant 1 and the entire elastic interchangeable insert unit 26 to the most favorable position for the prosthesis 18, the elastic interchangeable insert unit 26, and the submerged implant lower housing 1 via an orthodontic traction unit 40.

The use of a vertical stress gauge 29 as shown in FIG. 10 may be employed for the purpose of determining which elastic insert to select as a starting point. Said stress gauge comprises a laminated wafer which may be constructed of laminations of a low fusing thermoplastic compound of differing viscosity, the least easily deformable of which is located at the center of the wafer, and successively easier to displace layers of which progress outward. Each layer is color coded.

In this fashion, the wafer is placed over the prosthesis at the try in stage. The patient occludes on the wafer, which drives the prosthesis into the laminations, thus displacing the thermoplastic color coded material. The depth of penetration of the natural tooth abutments may be read as being either deeper than, the same as, or less than the depth of penetration over the implant teeth. The degree of vertical elasticity may be adjusted accordingly, until a uniform matching degree is achieved.

I claim:

1. A device for affixing a dental prosthesis to a jawbone, comprising:

a rigid biocompatible first cylindrical element having an open end and a closed end adapted to be inserted into the jawbone of a patient with the open end oriented toward the oral cavity, said first cylindrical element having a threaded interior;

an externally threaded second cylindrical element having a closed end and an open end, the second element being removably located within the first element with the external threads of the second element mating with the internal threads of the first element, said open end of said second element adapted to be oriented toward the oral cavity, said second element further comprising retentive protuberances located along the interior thereof;

a prosthesis support shaft located within said second element, said shaft comprising longitudinally oriented splines on an exterior surface thereof;

an annular limiter member, said limiter member comprising splines located along the interior and exterior thereof, said shaft extending through the interior of said limiter member with adjacent splines of the limiter member interior located between adjacent splines of the shaft.

2. A device as recited in claim 1, further comprising an elastic material located within said second element, said shaft and said limiter member being embedded within said elastic material, allowing said shaft to move through a prescribed envelope of motion.

3. A device as recited in claim 1, further comprising a tool for removing said second element, said shaft and said limiter member from said first element.

4. A device as recited in claim 3, wherein said tool comprises a wrench having an interior, said interior of said wrench further comprising splines which are adapted to engage between the splines of said shaft, to facilitate removal of said second element, said shaft and said limiter member.

5. A device as recited in claim 1, further comprising a spherical retaining globe, said globe located within said second element, an end of said shaft embedded within said globe.

6. A device as recited in claim 1, further comprising means for securing a prosthesis to said shaft.

7. A device as recited in claim 6, wherein said means for securing comprises a threaded member and said shaft further comprises a threaded bore, said threaded member being removably threaded in said bore.

8. A device as recited in claim 1, further comprising an orthodontic traction unit for aligning the device.

\* \* \* \* \*